(12) United States Patent
Ho

(10) Patent No.: US 9,259,500 B2
(45) Date of Patent: Feb. 16, 2016

(54) DEODORANT DISPENSER WITH AN ADJUSTABLE VOLATILE AREA

(76) Inventor: Yung-Wei Ho, Chia-Yi (TW)

( * ) Notice: Subject to any disclaimer, the term of this patent is extended or adjusted under 35 U.S.C. 154(b) by 441 days.

(21) Appl. No.: 13/567,449

(22) Filed: Aug. 6, 2012

(65) Prior Publication Data

US 2014/0034749 A1 Feb. 6, 2014

(51) Int. Cl.
*A61L 9/12* (2006.01)
(52) U.S. Cl.
CPC .................................... *A61L 9/127* (2013.01)
(58) Field of Classification Search
CPC ............ A61L 9/127; A61L 9/12; A61L 9/037; A61L 9/04; A01M 1/2044; A01M 1/2077
USPC .......... 239/34–60; 220/4.09, 4.06, 4.07, 4.05, 220/4.21, 87.1, 276, 256
See application file for complete search history.

(56) References Cited

U.S. PATENT DOCUMENTS

| | | | |
|---|---|---|---|
| 3,727,840 A | * | 4/1973 | Nigro ............................... 239/43 |
| 3,946,945 A | * | 3/1976 | Odioso et al. .................... 239/58 |
| 4,014,501 A | * | 3/1977 | Buckenmayer ................. 239/58 |
| 4,084,732 A | * | 4/1978 | Dearling ................... 222/402.17 |
| 4,258,004 A | * | 3/1981 | Valenzona et al. ............ 422/123 |
| 4,327,056 A | * | 4/1982 | Gaiser ........................... 422/124 |
| 4,372,490 A | * | 2/1983 | Le Caire et al. ................. 239/59 |

* cited by examiner

*Primary Examiner* — Arthur O Hall
*Assistant Examiner* — Chee-Chong Lee
(74) *Attorney, Agent, or Firm* — Symbus Law Group, LLC; Clifford D. Hyra

(57) ABSTRACT

A deodorant dispenser with an adjustable volatile area includes a body having a top plate. An annular wall extends from a bottom face of the top plate. A wall extension is connected to the annular wall by connecting portions and includes a slit. A post extends from the bottom face of the top plate and is surrounded by the annular wall. An absorber includes a tube having a central bole. The central bole receives the post of the body. A base includes a seat, an annular fence extending upward from a top face of the seat, and an engagement portion located in a center of the annular fence. The engagement portion of the base is tightly engaged with a bottom end of the post of the body. The wall extension can be torn away from the annular wall to increase an exposed area of the tube absorbing a liquid deodorant.

15 Claims, 2 Drawing Sheets

DEODORANT DISPENSER WITH AN ADJUSTABLE VOLATILE AREA

BACKGROUND OF THE INVENTION

The present invention relates to a deodorant dispenser and, more particularly, to a dispenser for dispensing a deodorant.

Deodorant dispensers are generally used to cover odors in places, such as toilets. Deodorants in the deodorant dispensers are either liquid or solid. A liquid deodorant dispenser generally includes a container receiving a liquid deodorant and an elongated cotton wick having an end submerged in the liquid deodorant. The other end of the cotton wick is connected to an absorber fixed to a cap that is mounted on an open end of the container. The absorber absorbs the liquid deodorant tinder capillary action. The fragrance passes through a plurality of adjustable openings in the cap into the air. However, such a liquid, deodorant dispenser has many components and, thus, is expensive. Furthermore, the openings of the cap merely allow adjustment in the amount of volatilization but not in the volatile area. A solid deodorant dispenser includes a solid deodorant that is formed by cooling of molten deodorant that was poured into a container with a cap. In use, the cap is removed such that a top face of the solid deodorant comes into contact with the air. Thus, the solid deodorant slowly volatilizes from top to bottom. However, the volatile area of the solid deodorant can not be adjusted according to needs.

Thus, a need exists for an inexpensive deodorant dispenser that can be adjusted in the volatile area according to needs.

BRIEF SUMMARY OF THE INVENTION

An objective of the present invention is to provide a deodorant dispenser that is adjustable in the volatile area.

The present invention fulfils the above objective by providing a deodorant dispenser with ah adjustable volatile area. The deodorant dispenser includes a body having a top plate. An annular wall extends from a bottom face of the top plate. A wall extension is connected to a lower face of the annular wall by a plurality of annularly spaced connecting portions. The wall extension includes a slit. A post extends from the bottom face of the top plate and is surrounded by the annular wall. An absorber includes a tube having a central hole. The central hole receives the post of the body. A base includes a seat, an annular fence extending upward from a top face of the seat, and an engagement portion located in a center of the annular fence. The engagement portion of the base is tightly engaged with a bottom end of the post of the body.

Preferably, the wall extension includes a protrusion at the slit.

Preferably, a thickness between the inner and outer peripheries of each connecting portion is smaller than a thickness between the inner and outer peripheries of the annular wall or smaller man a thickness between the inner and outer peripheries of the wall extension.

The present invention will become clearer in light of the following detailed description of illustrative embodiments of this invention described in connection with the drawings.

DETAILED DESCRIPTION OF THE INVENTION

Figure 1:
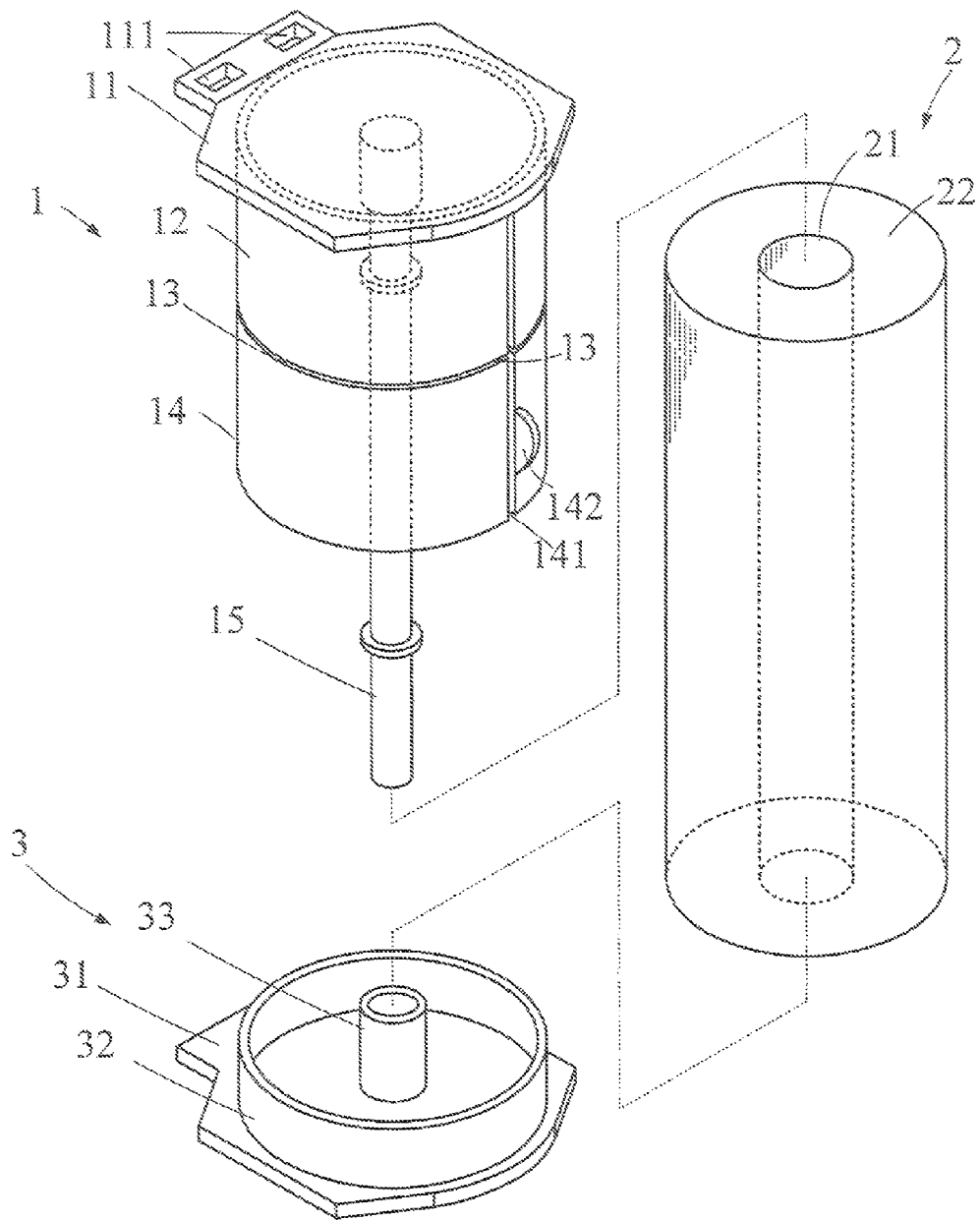
FIG 1. shows an exploded, perspective view of a deodorant dispenser with an adjustable volatile area according to the present invention.
Figure 2:
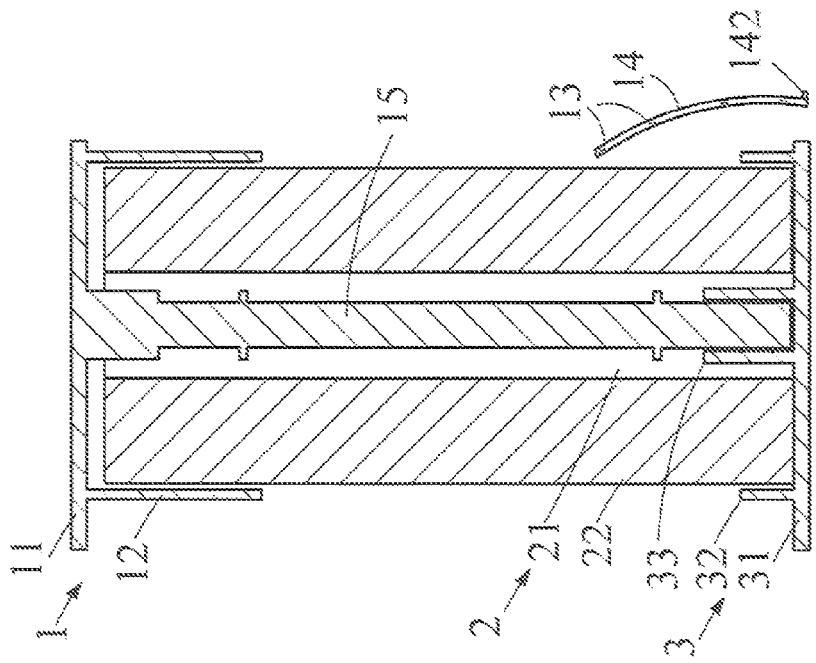
FIG. 2 shows a cross sectional view of the deodorant dispenser of FIG. 1.
Figure 3:
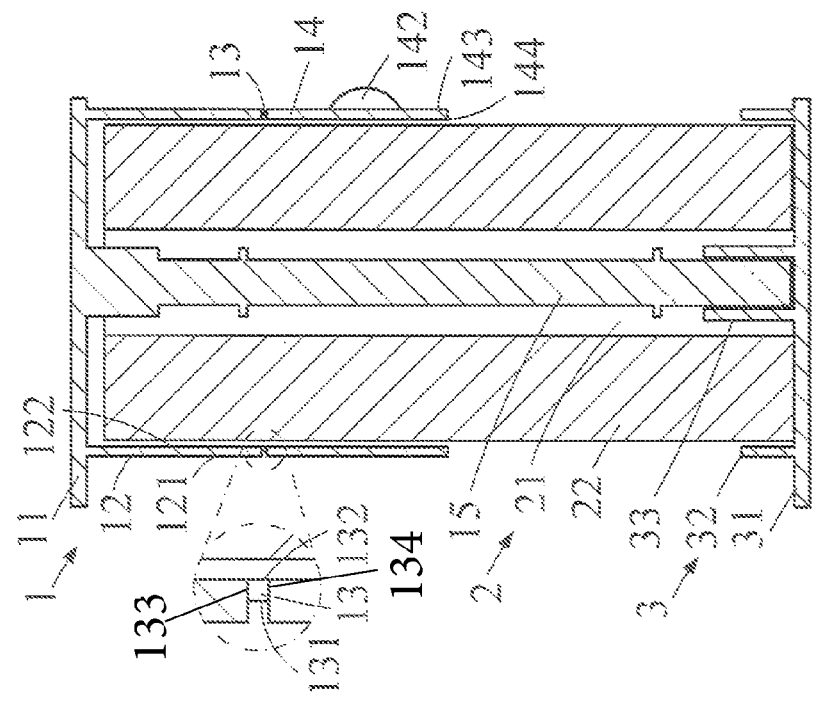
FIG. 3 shows a cross sectional view similar to FIG. 2, with a wall extension of the deodorant dispenser torn away.

A deodorant dispenser with an adjustable volatile area according to the present invention includes a body 1, an absorber 2, and a base 3. The body 1 includes a top plate 111 having at least one hanger hole 111. An annular wall 12 extends from a bottom face of the top plate 111. A wall extension 14 is connected to a lower face of the annular wall 12 by a plurality of annularly spaced connecting portions 13. The wall extension 14 includes a slit 141. A post 15 extends from the bottom face of the top plate 111 and is surrounded by the annular wall 12 and the wall extension 14. Preferably, the wall extension 14 includes a protrusion 142 at the slit 141 to allow easy grip for tearing the wall extension 14 from the annular wall 12. Preferably, a thickness between the inner and outer peripheries 132, 131 of each connecting portion 13 is smaller than a thickness between the inner and outer peripheries 122, 121 of the annular wall 12 or smaller than a thickness between the inner and outer peripheries 144, 143 of the wall extension 14, allowing the wall extension 14 to be easily torn away from the annular wall 12. Each connecting portion 13 has a top face 133 touching the annular wall 12 and a bottom face 134 touching the wall extension 14 and the inner and outer peripheries 132, 131 of each connecting portion do not touch the wall extension 14 or annular wall 12 except at their top and bottom.

The absorber 2 includes a tube 22 made of a porous material, such as polyvinyl acetate (PVA). Thus, the tube 22 can absorb more liquid deodorant. The tube 22 includes a central hole 21 receiving the post 15 of the body 1.

The base 3 includes a seat 31. An annular fence 32 extends upward from a top face of the seat 31. An engagement portion 33 is located in a center of the annular fence 32 and tightly engaged with a bottom end of the post 15 of the body 1. Thus, the tube 22 mounted around the post 15 of the body 1 is fixed between the base 3 and the body 1. The annular fence 32 on the base 3 can receive a liquid deodorant or prevent dripping of the liquid deodorant absorbed by the absorber 2.

In a small place or the odor is not so bad, the wall extension 14 can be kept on the annular wall 12, such that the tube 22 absorbing the liquid deodorant has a less exposed area contacting the air.

In a larger space or the odor is bad, the wall extension 14 can be torn away from the annular wall 12, such that the tube 22 absorbing the liquid deodorant has a larger exposed area contacting the air.

Although specific embodiments have been illustrated and described, numerous modifications and variations are still possible without departing from the essence of the invention. The scope of the invention is limited by the accompanying claims.

The invention claimed is:

1. A deodorant dispenser comprising:
   a body including a top plate having a bottom face, with an annular wall extending from the bottom face of the top plate and having a lower face, with a wall extension connected to the lower face of the annular wall by a plurality of annularly spaced connecting portions, with the wall extension including a slit, and a post extending from the bottom face of the top plate, with the post surrounded by the annular wall;
   an absorber including a tube having a central hole, with the central hole receiving the post of the body; and a base including a seat having a top face, an annular fence extending upward from the top face of the seat, and an engagement portion located in a center of the annular fence, with the engagement portion of the base tightly engaged with a bottom end of the post of the body;

wherein the annular wall and the wall extension enclose the absorber by limiting an exposed area of the tube, and wherein the dispenser is configured so that, when the wall extension is torn away from the annular wall, leaving the rest of the dispenser intact, the exposed area of the tube absorbing a liquid deodorant is increased.

2. The deodorant dispenser as claimed in claim 1, with the wall extension including a protrusion at the slit.

3. The deodorant dispenser as claimed in claim 1, with each of the annularly spaced connecting portions and the annular wall including an inner periphery and an outer periphery, with a thickness between the inner and outer peripheries of each of the plurality of connecting portions being smaller than a thickness between the inner and outer peripheries of the annular wall.

4. The deodorant dispenser as claimed in claim 1, with each of the annularly spaced connecting portions and the wall extension including an inner periphery and an outer periphery, with a thickness between the inner and outer peripheries of each of the plurality of connecting portions being smaller than a thickness between the inner and outer peripheries of the wall extension.

5. The deodorant dispenser as claimed in claim 1, wherein the wall extension extends away from the annular wall.

6. The deodorant dispenser as claimed in claim 1, wherein the wall extension has the same inner radius as the annular wall.

7. The deodorant dispenser as claimed in claim 1, wherein at least one of the annularly spaced connecting portions has an inner periphery that is a distance away from the axis of the annular wall, where the distance away from the axis of the annular wall is equal to an inner radius of the annular wall.

8. The deodorant dispenser as claimed in claim 1, wherein the slit extends all the way through the wall extension, creating an opening.

9. The deodorant dispenser as claimed in claim 1, wherein the wall extension extends downward from the annular wall.

10. The deodorant dispenser as claimed in claim 1, wherein the annularly spaced connecting portions are disposed between the lower face of the annular wall and the wall extension.

11. The deodorant dispenser as claimed in claim 10, wherein the wall extension extends downward from a lower face of each annularly spaced connecting portion.

12. The deodorant dispenser as claimed in claim 10, wherein the annular wall does not touch the wall extension.

13. The deodorant dispenser as claimed in claim 10, wherein the annularly spaced connecting portions each comprise a top face and a bottom face, wherein the top face of each annularly spaced connecting portion touches the lower face of the annular wall and the bottom face of each annularly spaced connecting portion touches an upper face of the wall extension.

14. The deodorant dispenser as claimed in claim 12, wherein the annular wall does not touch the wall extension and the inner and outer peripheries of the annularly spaced connecting portions do not touch the annular wall or the wall extension, except at their tops and bottoms.

15. The deodorant dispenser as claimed in claim 1, wherein there is only one slit and the wall extension forms a complete ring except for the slit.

\* \* \* \* \*